US006699871B2

(12) United States Patent
Edmondson et al.

(10) Patent No.: US 6,699,871 B2
(45) Date of Patent: Mar. 2, 2004

(54) BETA-AMINO HETEROCYCLIC DIPEPTIDYL PEPTIDASE INHIBITORS FOR THE TREATMENT OR PREVENTION OF DIABETES

(75) Inventors: Scott D. Edmondson, New York, NJ (US); Michael H. Fisher, Ringoes, NJ (US); Dooseop Kim, Westfield, NJ (US); Malcolm Maccoss, Freehold, NJ (US); Emma R. Parmee, Scotch Plains, NJ (US); Ann E. Weber, Scotch Plains, NJ (US); Jinyou Xu, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 21 days.

(21) Appl. No.: 10/189,603

(22) Filed: Jul. 5, 2002

(65) Prior Publication Data

US 2003/0100563 A1 May 29, 2003

Related U.S. Application Data

(60) Provisional application No. 60/303,474, filed on Jul. 6, 2001.

(51) Int. Cl.$^7$ .................. C07D 487/04; A61K 31/4985; A61P 3/04; A61P 3/10
(52) U.S. Cl. ......................................... 514/249; 544/350
(58) Field of Search ........................... 544/350; 514/249

(56) References Cited

U.S. PATENT DOCUMENTS

| 5,939,560 A | 8/1999 | Jenkins et al. ............... 548/535 |
| 6,166,063 A | 12/2000 | Villhauer ..................... 514/423 |
| 6,303,661 B1 | 10/2001 | Demuth et al. .............. 514/866 |

FOREIGN PATENT DOCUMENTS

| WO | WO 97/40832 | 11/1997 |
| WO | WO 98/19998 | 5/1998 |
| WO | WO 00/34241 | 6/2000 |
| WO | WO 01/34594 A1 | 5/2001 |
| WO | WO 01/96295 A3 | 12/2001 |
| WO | WO 01/96295 A2 | 12/2001 |
| WO | WO 02/02560 A2 | 1/2002 |

OTHER PUBLICATIONS

"Novel N–substituted–2–cyanopyrrolidines as potent inhibitors of dipeptidyl peptidase IV in the treatment of non–insulin–dependent diabetes mellitus", Exp. Opin, Ther. Patents, 10(12), pp. 1937–1942 (2000).

Ashworth, et al., "2–Cyanopyrrolidides as Potent, Stable Inhibitors of Dipeptidyl Peptidase IV", Bioorg. Med. Chem. Lett., vol. 6, No. 10, pp. 1163–1166, (1996).

Ashworth, et al., "4–Cyanothiazolidides as Very Potent, Stable Inhibitors of Dipeptidyl Peptidase IV", Bioorg. Med. Chem. Lett., vol. 6, No. 22, pp. 2745–2748, (1996).

Deacon, et al., "Dipeptidyl peptidase IV inhibition as an approach to the treatment and prevention of type 2 diabetes: a historical perspective", Biochem. Biophys. Res. Commun. vol. 294, pp. 1–4 (2002).

*Primary Examiner*—Mark L. Berch
*Assistant Examiner*—Kahsay Habte
(74) *Attorney, Agent, or Firm*—Philippe L. Durette; Melvin Winokur; J. Eric Thies

(57) ABSTRACT

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

26 Claims, No Drawings

BETA-AMINO HETEROCYCLIC DIPEPTIDYL PEPTIDASE INHIBITORS FOR THE TREATMENT OR PREVENTION OF DIABETES

CROSS REFERENCE TO RELATED APPLICATIONS

This application claims priority under 35 U.S.C. §119(e) from Serial No. 60/303,474, filed Jul. 6, 2001.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6(10), 1163–1166 (1996); and Bioorg. Med. Chem. Lett., 6(22), 2745–2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions.

SUMMARY OF THE INVENTION

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention is directed to compounds of the formula I:

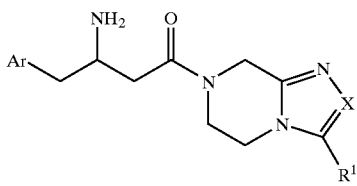

I wherein:
- Ar is phenyl which is unsubstituted or substituted with 1–5 of $R^3$, wherein $R^3$ is independently selected from the group consisting of:
  - (1) halogen,
  - (2) $C_{1-6}$alkyl, which is linear or branched and is unsubstituted or substituted with 1–5 halogens,
  - (3) $OC_{1-6}$alkyl, which is linear or branched and is unsubstituted or substituted with 1–5 halogens, and
  - (4) CN;
- X is selected from the group consisting of:
  - (1) N, and
  - (2) $CR^2$;
- $R^1$ and $R^2$ are independently selected from the group consisting of:
  - (1) hydrogen,
  - (2) CN,
  - (3) $C_{1-10}$alkyl, which is linear or branched and which is unsubstituted or substituted with 1–5 halogens or phenyl, which is unsubstituted or substituted with 1–5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched,
  - (4) phenyl which is unsubstituted or substituted with 1–5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched, and
  - (6) a 5- or 6-membered heterocycle which may be saturated or unsaturated comprising 1–4 heteroatoms independently selected from N, S and O, the heterocycle being unsubstituted or substituted with 1–3 substituents independently selected from oxo, OH, halogen, $C_{1-6}$alkyl, and $OC_{1-6}$alkyl, wherein the $C_{1-6}$alkyl and $OC_{1-6}$alkyl are linear or branched and optionally substituted with 1–5 halogens;
- $R^4$ is $C_{1-6}$alkyl, which is linear or branched and which is unsubstituted or substituted with 1–5 groups independently selected from halogen, $CO_2H$, and $CO_2C_{1-6}$alkyl, wherein the $CO_2C_{1-6}$alkyl is linear or branched;

and pharmaceutically acceptable salts thereof and individual diastereomers thereof.

An embodiment of the present invention includes compounds of the formula Ia:

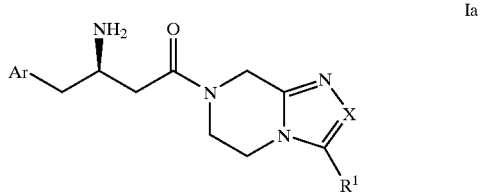

Ia wherein X, Ar and $R^1$ are defined herein;
and pharmaceutically acceptable salts and individual diastereomers thereof.

Another embodiment of the present invention includes compounds of the formula Ib:

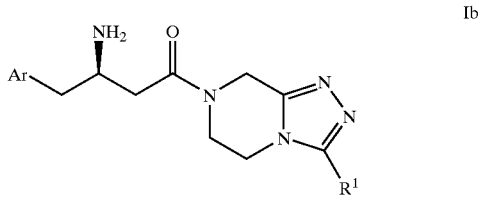

Ib wherein Ar and $R^1$ are defined herein;
and pharmaceutically acceptable salts and individual diastereomers thereof.

Another embodiment of the present invention includes compounds of the formula Ic:

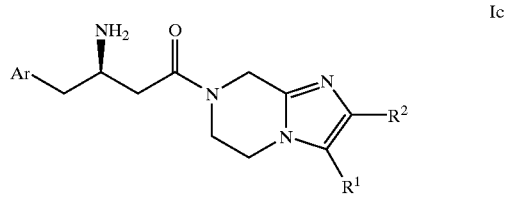

Ic wherein Ar, $R^1$ and $R^2$ are defined herein;
and pharmaceutically acceptable salts thereof and individual diastereomers thereof.

In the present invention it is preferred that Ar is phenyl which is unsubstituted or substituted with 1–5 substitutents which are independently selected from the group consisting of:
- (1) fluoro,
- (2) bromo, and
- (3) $CF_3$.

In the present invention it is more preferred that Ar is selected from the group consisting of:
- (1) phenyl,
- (2) 2-fluorophenyl,
- (3) 3,4-difluorophenyl,
- (4) 2,5-difluorophenyl,
- (5) 2,4,5-trifluorophenyl,
- (6) 2-fluoro-4-(triflouromethyl)phenyl, and
- (7) 4-bromo-2,5-difluorophenyl.

In the present invention it is preferred that $R^1$ is selected from the group consisting of:
- (1) hydrogen, and
- (2) $C_{1-6}$alkyl, which is linear or branched and which is unsubstituted or substituted with phenyl or 1–5 fluoro.

In the present invention it is more preferred that $R^1$ is selected from the group consisting of:
(1) hydrogen,
(2) methyl,
(3) ethyl,
(4) $CF_3$,
(5) $CH_2CF_3$,
(5) $CF_2CF_3$
(6) phenyl, and
(7) benzyl.

In the present invention it is more preferred that $R^1$ is selected from the group consisting of:
(1) hydrogen,
(2) methyl,
(3) ethyl,
(4) $CF_3$, and
(5) $CH_2CF_3$.

In the present invention it is even more preferred that $R^1$ is hydrogen or $CF_3$.

In the present invention it is preferred that $R^2$ is selected from:
(1) hydrogen,
(2) $C_{1-6}$alkyl, which is linear or branched and which is unsubstituted or substituted with 1–5 fluoro,
(3) phenyl, which is unsubstituted or substituted with 1–3 substituents independently selected from fluoro, $OCH_3$, and $OCF_3$.

In the present invention it is more preferred that $R^2$ is selected from the group consisting of:
(1) hydrogen,
(2) methyl,
(3) ethyl,
(4) $CF_3$,
(5) $CH_2CF_3$,
(5) $CF_2CF_3$
(6) phenyl,
(7) (4-methoxy)phenyl,
(8) (4-trifluoromethoxy)phenyl,
(9) 4-fluorophenyl, and
(10) 3,4-difluorophenyl.

In the present invention it is even more preferred that $R^2$ is $CF_3$ or $CF_2F_3$.

In the present invention it is preferred that $R^3$ is F, Br or $CF_3$.

The compounds of the present invention may contain one or more asymmetric centers and can thus occur as racemates and racemic mixtures, single enantiomers, diastereomeric mixtures and individual diastereomers. The compounds of the instant invention have one asymmetric center at the beta carbon atom. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom that is attached to the amine group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

It will be understood that, as used herein, references to the compounds of Formula I are meant to also include the pharmaceutically acceptable salts.

As appreciated by those of skill in the art, halo or halogen as used herein are intended to include fluoro, chloro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. A group which is designated as being independently substituted with substituents may be independently substituted with multiple numbers of such substituents. The term "heterocycle" as used herein is intended to include 5- or 6-membered ring systems which are within the following listing: benzimidazolyl, benzodioxanyl, benzofuranyl, benzopyrazolyl, benzothiadiazolyl, benzotriazolyl, benzothiophenyl, benzoxadiazolyl, benzoxazolyl, carbazolyl, carbolinyl, chromanyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolinyl, quinoxalinyl, tetrazolyl, thiadiazolyl, thiazolidinyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydroimidazolyl, tetrahydroisoquinolinyl, and tetrahydrothienyl.

Exemplifying the invention is the use of the compounds disclosed in the Examples and herein.

Specific compounds within the present invention include a compound which selected from the group consisting of the compounds disclosed in the following Examples and pharmaceutically acceptable salts thereof and individual diastereomers thereof.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutical carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m=50$ $\mu$M; $k_{cat}=75$ s$^{-1}$; $k_{cat}/K_m=1.5\times10^6$ M$^{-1}$s$^{-1}$. A typical reaction contains approximately 50 pM enzyme, 50 $\mu$M Gly-Pro-AMC, and buffer (100 mM HEPES, pH 7.5, 0.1 mg/ml BSA) in a total reaction volume of 100 $\mu$l. Liberation of AMC is monitored continuously in a 96-well plate fluorometer using an excitation wavelength of 360 nm and an emission wavelength of 460 nm. Under these conditions, approximately 0.8 $\mu$M AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 μM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP, glucagon). Inactivation of these peptides by DP-IV may also play a role in glucose homeostasis.

The DP-IV inhibitors of the present invention therefore have utility in the treatment of type II diabetes and in the treatment and prevention of the numerous conditions that often accompany Type II diabetes, including metabolic syndrome X, reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (Am. J. Physiol. 277, R910–R916 (1999)). ICV administration of GLP-1 in rats and mice also has profound effects on food intake (Nature Medicine 2, 1254–1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (Nature Medicine 6, 802–807 (2000)).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (BBA 1122, 147–153 (1992)); (2) GRF is rapidly degraded in plasma to GRF[3-44]; this is prevented by the DP-IV inhibitor diprotin A; and (3) GRF[3-44] is found in the plasma of a human GRF transgenic pig (J. Clin. Invest. 83, 1533–1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (Regulatory Peptides 90, 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosponate), an irreversible inhibitor of DP-IV, was shown to double cardiac allograft survival in rats from day 7 to day 14 (Transplantation 63, 1495–1500 (1997)). DP-IV inhibitors have been tested in collagen and alkyldiamine-induced arthritis in rats and showed a statistically significant attenuation of hind paw swelling in this model (Int. J. Immunopharmacology 19, 15–24 (1997), Immunopharmacology 40, 21–26 (1998)). DP-IV is upregulated in a number of autoimmune diseases including rheumatoid arthritis, multiple sclerosis, Graves' disease, and Hashimoto's thyroiditis (Immunology Today 20, 367–375 (1999)).

HIV Infection: DP-IV inhibition may be useful for the treatment or prevention of HIV infection or AIDS because a number of chemokines which inhibit HIV cell entry are potential substrates for DP-IV (Immunology Today 20, 367–375 (1999)). In the case of SDF-1alpha, cleavage decreases antiviral activity (PNAS 95, 6331-6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m \sim 10^6$ $M^{-1}s^{-1}$ or greater. In an electric shock jump test model of analgesia in rats, a DP-IV inhibitor showed a significant effect that was independent of the presence of exogenous endomorphin-2 (Brain Research 815, 278–286 (1999)).

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (J. Exp. Med. 190, 301–305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (Eur. J. Clin. Chem. Clin. Biochem 30, 333–338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (Eur. J. Clin. Chem. Clin. Biochem 30, 333–338 (1992)).

Gingivitis: DP-IV inhibition may be useful for the treatment of gingivitis because DP-IV activity was found in gingival crevicular fluid and in some studies correlated with periodontal disease severity (Arch. Oral Biol. 37, 167–173 (1992)).

Osteoporosis: DP-IV inhibition may be useful for the treatment or prevention of osteoporosis because GIP receptors are present in osteoblasts.

Tthe compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues such as tolbutamide and glipizide, meglitinide, and related materials;

(e) α-glucosidase inhibitors (such as acarbose);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide Y5 inhibitors, and $\beta_3$ adrenergic receptor agonists;

(m) an ileal bile acid transporter inhibitor; and (n) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and anti-obesity compounds.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted heterocyclic intermediates such as those of formula III, using standard peptide coupling conditions followed by deprotection. The preparation of these intermediates is described in the following schemes.

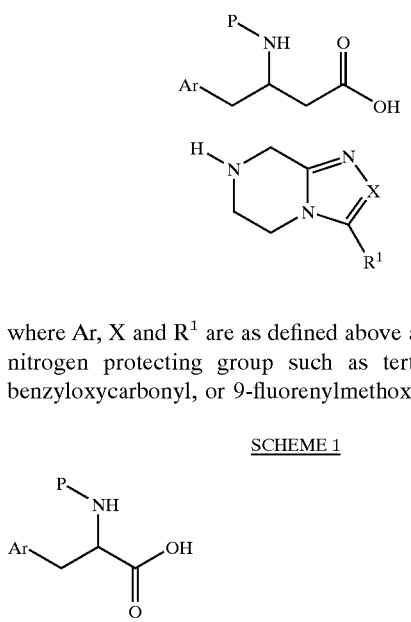

where Ar, X and $R^1$ are as defined above and P is a suitable nitrogen protecting group such as tert-butoxycarbonyl, benzyloxycarbonyl, or 9-fluorenylmethoxycarbonyl.

SCHEME 1

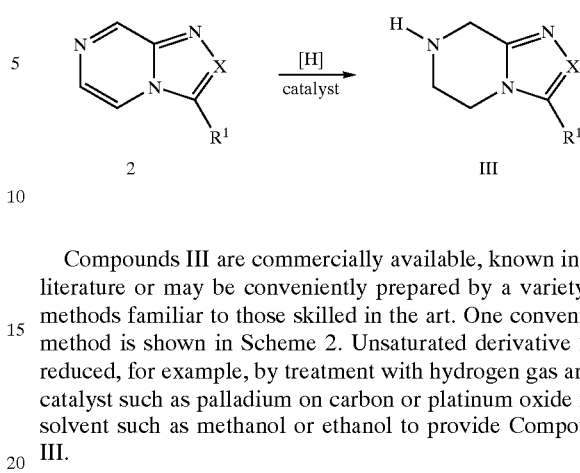

Compounds of formula II are commercially available, known in the literature or may be conveniently prepared by a variety of methods familiar to those skilled in the art. One common route is illustrated in Scheme 1. Acid 1, which may be commercially available or readily prepared from the corresponding amino acid by protection using, for example, di-tert-butyl-dicarbonate (for P=Boc), carbobenzyloxy chloride (for P=Cbz), or N-(9-fluorenylmethoxycarbonyloxy) succinimide (for P=Fmoc), is treated with isobutyl chloroformate and a base such as triethylamine or diisopropylethylamine, followed by diazomethane. The resultant diazoketone is then treated with silver benzoate in a solvent such as methanol or aqueous dioxane and may be subjected to sonication following the procedure of Sewald et al., *Synthesis,* 837 (1997) in order to provide the beta amino acid II. As will be understood by those skilled in the art, for the preparation of enantiomerically pure beta amino acids II, enantiomerically pure alpha amino acids 1 may be used. Alternate routes to these compounds can be found in the following reviews: E. Juaristi, *Enantioselective Synthesis of β-Amino Acids,* Ed., Wiley-VCH, New York: 1997, Juaristi et al., *Aldrichimica Acta,* 27, 3 (1994), Cole et al., *Tetrahedron,* 32, 9517 (1994).

SCHEME 2

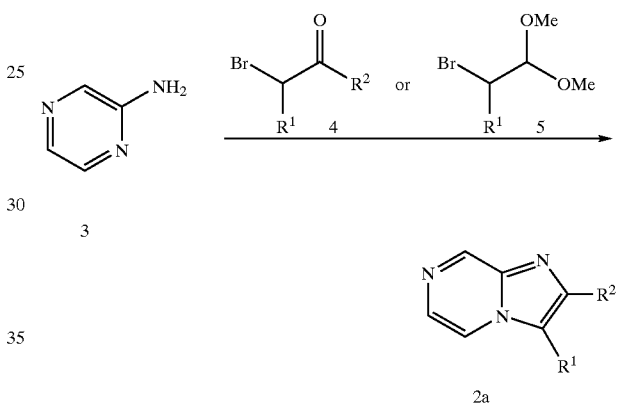

Compounds III are commercially available, known in the literature or may be conveniently prepared by a variety of methods familiar to those skilled in the art. One convenient method is shown in Scheme 2. Unsaturated derivative 2 is reduced, for example, by treatment with hydrogen gas and a catalyst such as palladium on carbon or platinum oxide in a solvent such as methanol or ethanol to provide Compound III.

SCHEME 3

Intermediates 2, from Scheme 2, are themselves commercially available, known in the literature or may be conveniently prepared by a variety of methods familiar to those skilled in the art. One such method when X is $CR^2$ is illustrated in Scheme 3. Aminopyrazine 3 is treated with a 2-haloketone such as 2-bromoketone 4 in a solvent such as methanol or ethanol to provide intermediate 2a. Alternatively, for the preparation of intermediate 2a where $R^2$ is H, 2-bromo-dimethylacetal 5 and a catalytic amount of acid such as hydrochloric acid may be employed instead of intermediate 4.

SCHEME 4

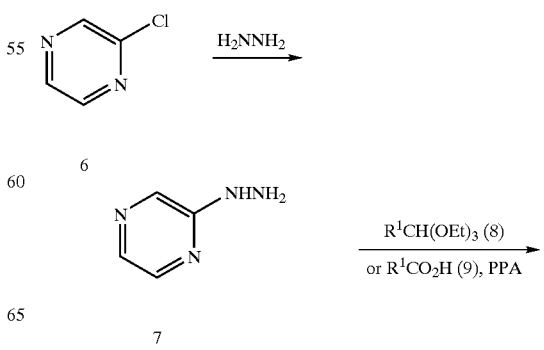

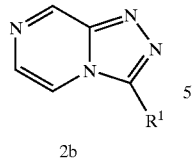

2b

A convenient method for the preparation of intermediate 2b, where X is N, is illustrated in Scheme 4. Chloropyrazine 6 is treated with hydrazine to provide hydrazinopyrazine 7. Compound 7 may be condensed with either an orthoester such as triethyl orthoester 8 to give 2b or with a carboxylic acid 9 in polyphosphoric acid at elevated temperatures to give 2b.

SCHEME 5

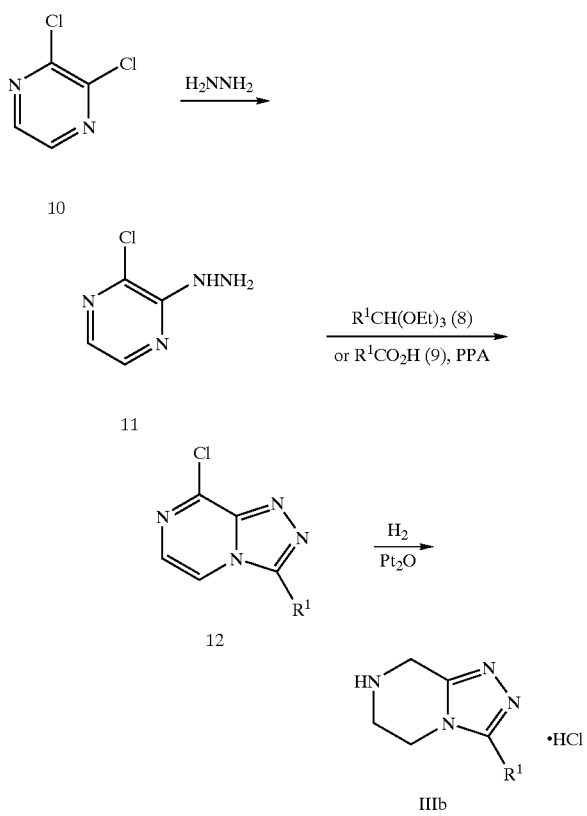

An alternate route for the preparation of Compound IIIb wherein X is N is illustrated in Scheme 5. Compound 12 is prepared according to the method outlined above employing dichloropyrazine 10 instead of chloropyrazine 6. Compound 12 is then subjected to catalytic hydrogenation using a catalyst such as platinum oxide to provide Compound IIIb, as its monohydrochloride salt.

SCHEME 6

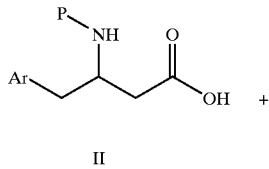

II

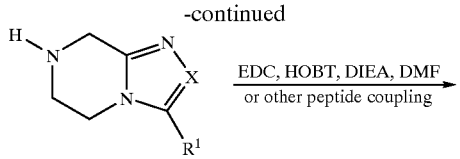

III

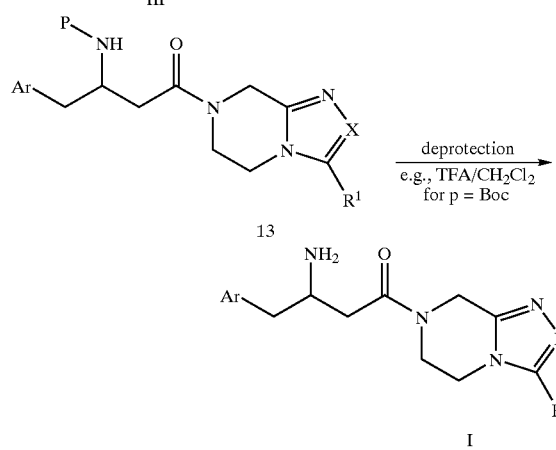

Intermediates II and III are coupled under standard peptide coupling conditions, for example, using 1-ethyl-3-(3-dimethylaminopropyl)carbodiimide (EDC), 1-hydroxybenzotriazole (HOBT), and a base, generally diisopropylethylamine, in a solvent such as N,N-dimethylformamide (DMF) or dichloromethane for 3 to 48 hours at ambient temperature to provide intermediate 13 as shown in Scheme 6. The protecting group is then removed with, for example, trifluoroacetic acid or methanolic hydrogen chloride in the case of Boc to give the desired amine I. The product is purified from unwanted side products, if necessary, by recrystallization, trituration, preparative thin layer chromatography, flash chromatography on silica gel as described by W. C. Still et al, *J. Org. Chem.*, 43, 2923 (1978), or HPLC. Compounds which are purified by HPLC may be isolated as the corresponding salt. Purification of intermediates is achieved in the same manner.

In some cases the intermediate 13 from the coupling reaction described in Scheme 6 may be further modified before removal of the protecting group, for example, by manipulation of substituents on X or $R^1$. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

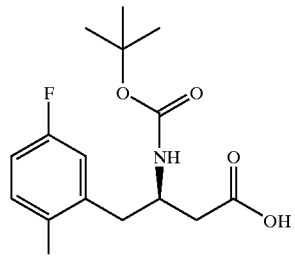

(3R)-3-[(1,1-Dimethylethoxycarbonyl)amino]-4-(2,5-difluorophenyl)butanoic Acid Step A. (R,S)-N-(1,1-Dimethylethoxycarbonyl)-2,5-difluorophenylalanine To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and brine, dried over magnesium sulfate and concentrated in vacuo. The crude material was purified by flash chromatography (silica gel, 97:2:1 dichloromethane:methanol:acetic acid) to afford 671 mg of the title compound. MS 302 (M+1).

Step B. (R,S)-3-[(1,1-Dimethylethoxycarbonyl)amino]-1-diazo-4-(2,5-difluoro-phenyl)butan-2-one To a solution of 2.23 g (7.4 mmol) of (R,S)-N-(1,1-dimethylethoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded 1.5 g of diazoketone. $^1$H NMR (500 MHz, CDCl$_3$) δ 7.03–6.95 (m, 1H), 6.95–6.88 (m, 2H), 5.43 (bs, 1H), 5.18 (bs, 1H), 4.45 (bs, 1H), 3.19–3.12 (m, 1H), 2.97–2.80 (m, 1H), 1.38 (s, 9H).

Step C. (3R)-3-[(1,1-Dimethylethoxycarbonyl)amino]-4-(2,5-difluorophenyl)butanoic Acid To a solution of 2.14 g (6.58 mmol) of (R,S)-3-[(1,1-dimethylethoxycarbonyl)-amino]-1-diazo-4-(2,5-difluorophenyl)butan-2-one dissolved in 100 mL of methanol at −30° C. were added sequentially 3.3 mL (19 mmol) of diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol:1N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 360 mg of the title compound as a white foamy solid. $^1$H NMR (500 MHz, CDCl$_3$) δ 7.21 (m, 1H), 6.98 (m, 2H), 6.10 (bs, 1H), 5.05 (m,1H), 4.21 (m, 1H), 2.98 (m, 2H), 2.60 (m, 2H), 1.38 (s, 9H).

INTERMEDIATE 2

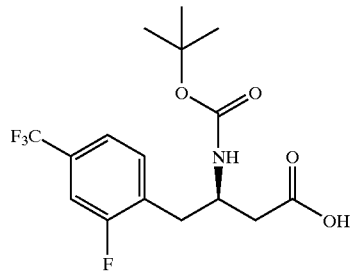

(3R)-3-[(1,1-Dimethylethoxycarbonyl)amino]-4-[2-fluoro-4-(trifluoromethyl)phenyl]-butanoic Acid Step A. (2R,5S)-2,5-Dihydro-3,6-dimethoxy-2-(2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (19.5 mmol) of 2-fluoro-4-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0–5% ethyl acetate in hexanes) afforded 5.5 g of the title compound. $^1$H NMR (500 MHz, CDCl$_3$) δ 7.33–7.25 (m, 3H), 4.35–4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25–2.15 (m, 1H), 1.0 (d, 3H, J=7 Hz), 0.66 (d, 3H, J=7 Hz).

Step B. (R)-N-(1,1-Dimethylethoxycarbonyl)-2-fluoro-4-trifluoromethyl)phenyl-alanine Methyl Ester To a solution of 5.5 g (15 mmol) of (2R,5S)-2,5-dihydro-3,6-dimethoxy-2-(2'-fluoro-4'-(trifluoromethyl)benzyl)-5-isopropylpyrazine in 50 mL of a mixture of acetonitrile:dichloromethane (10:1) was added 80 mL of 1N aqueous trifluoroacetic acid. The reaction was stirred for 6 h and the organic solvents were removed in vacuo. Sodium carbonate was added until the solution was basic (>pH 8), and then the reaction was diluted with 100 mL of tetrahydrofuran and 10 g (46 mmol) of di-tert-butyl dicarbonate was added. The resulting slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded 5.1 g of the title compound. $^1$H NMR (500 MHz, CDCl$_3$) δ 7.38–7.28 (m, 3H), 5.10 (bd, 1H), 4.65–3.98 (m, 1H), 3.76 (s, 3H), 3.32–3.25 (m, 1H), 3.13–3.05 (m, 1H), 1.40 (s, 9H).

Step C. (R)-N-(1,1-Dimethylethoxycarbonyl)-2-fluoro-4-trifluoromethyl)phenyl-alanine A solution of 5.1 g (14 mmol) of (R,S)-N-(1,1-dimethylethoxycarbonyl)-2-fluoro-4-trifluoromethyl) phenylalanine methyl ester in 350 mL of a mixture of tetrahydrofuran: methanol:1N lithium hydroxide (3:1:1) was stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 4.8 g of the title compound. $^1$H NMR (500 MHz, CD$_3$OD) δ 7.45–7.38 (m, 3H), 4.44–4.40 (m, 1H), 3.38–3.33 (m, 1H), 2.98 (dd, 1H, J=9.6, 13.5 Hz), 1.44 (s, 9H).

Step D. (3R)-3-[(1,1-Dimethylethoxycarbonyl)amino]-4-[2-fluoro-4-(trifluoromethyl)-phenyl]butanoic acid To a solution of 3.4 g (9.7 mmol) of the product from Step C in 60 mL of tetrahydrofuran at 0° C. were added sequentially 2.3 mL (13 mmol) of diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane:ethyl acetate) afforded 0.5 g of diazoketone. To a solution of 0.5 g (1.33 mmol) of the diazoketone dissolved in 100 mL of methanol at 0° C. were added sequentially 0.7 mL (4 mmol) of diisopropylethylamine and 32 mg (0.13 mmol) of silver benzoate. The reaction was stirred for 2 h before diluting with ethyl acetate and washing sequentially with 2N hydrochloric acid, saturated aqueous sodium bicarbonate, and brine. The organic phase was dried over magnesium sulfate, concentrated in vacuo and dissolved in 50 mL of a mixture of tetrahydrofuran:methanol:1N aqueous lithium hydroxide (3:1:1) and stirred at 50° C. for 3 h. The reaction was cooled, acidified with 5% dilute hydrochloric acid and extracted with ethyl acetate. The combined organic phases were washed with brine, dried over magnesium sulfate and concentrated in vacuo to give 410 mg of the title compound as a white foamy solid. $^1$H NMR (500 MHz, CD$_3$OD) δ 7.47–7.33 (m, 3H), 4.88 (bs, 1H), 4.26–3.98 (m, 1H), 3.06–3.01 (m, 1H), 2.83–2.77 (m, 1H), 2.58–2.50 (m, 2H), 1.29 (s, 9H).

INTERMEDIATE 3

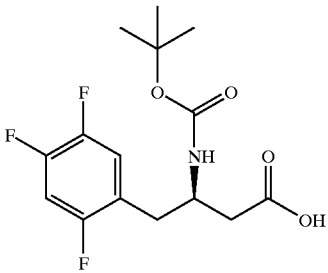

(3R)-3-[(1,1-Dimethylethoxycarbonyl)amino]-4-(2,4,5-trifluorophenyl)butanoic Acid Step A. (2S, 5R)-2,5-Dihydro-3,6-dimethoxy-2-isopropyl-5-(2',4',5'trifluorobenzyl)-pyrazine The title compound (3.81 g) was prepared from 3.42 g (18.5 mmol) of (2S)-2,5-dihydro-3,6-dimethoxy-2-isopropylpyrazine using the procedure described for Intermediate 2, Step A. 1H NMR (500 MHz, CDCl$_3$) δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz), 0.62 (d, 3H, J=8 Hz).

Step B. (R)-N-(1,1-Dimethylethoxycarbonyl)-2,4,5-trifluorophenylalanine Methyl Ester To a solution of 3.81 g (11.6 mmol) of (2S, 5R)-2,5-dihydro-3,6-dimethoxy-2-isopropyl-5-(2',4',5'trifluorobenzyl)pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyldicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford 2.41 g of the title compound. $^1$H NMR (500 MHz, CDCl$_3$) δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C. (R)-N-(1,1-Dimethylethoxycarbonyl)-2,4,5-trifluorophenylalanine

The title compound (2.01 g) was prepared from 2.41 g (7.5 mol) of (R)-N-(1,1-dimethylethoxycarbonyl)-2,4,5-trifluorophenylalanine methyl ester using the procedure described for Intermediate 2, Step C. MS (M+1)-BOC 220.9.

Step D. (3R)-3-[(1,1-Dimethylethoxycarbonyl)amino]-4-(2,4,5-trifluorophenyl)-butanoic Acid To a solution of 0.37 g (1.16 mmol) of (R)-N-(1,1-dimethylethoxycarbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane:water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded 401 mg of the title compound. $^1$H NMR (500 MHz, CDCl$_3$) δ 7.06 (m, 1H), 6.95 (m, 1H), 5.06 (bs, 1H), 4.18 (m, 1H), 2.98 (m, 2H), 2.61 (m, 2H), 1.39 (s, 9H).

INTERMEDIATE 4

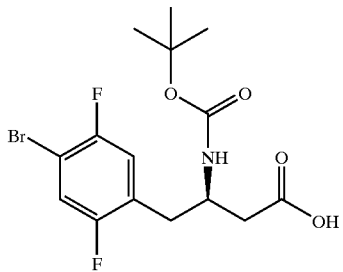

(3R)-3-[(1,1-Dimethylethoxycarbonyl)amino]-4-(4-bromo-2,5-difluorophenyl)-butanoic Acid Step A. 4-Bromo-2,5-difluorobenzyl Bromide To a solution of 2 g (8.44 mmol) of 4-bromo-2,5-difluorobenzoic acid (prepared according to the procedure of Ishikawa et al., *Kogyo Kagaku Zasshi*, pg 972–979, 1970) in 20 mL of tetrahydrofuran was added 40 mL of a 1M solution of borane-tetrahydrofuran complex. The solution was heated under reflux for 64 h, cooled to ambient temperature and 100 mL of methanol was added. The reaction was then heated for a further 2 h, cooled and concentrated in vacuo. Purification by flash chromatography (silica gel, 9:1 hexane:ethyl acetate) afforded 1.6 g of 4-bromo-2,5-difluorobenzyl alcohol. To a solution of 1.3 g (5.6 mmol) of 4-bromo-2,5-difluorobenzyl alcohol in 20 mL of dichloromethane at 0° C. was added 2.27 g (6.7 mmol) of carbon tetrabromide and 1.8 g (6.7 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 9:1 hexane:ethyl acetate) to afford 1.5 g of the title compound.

Step B. (2S, 5R)-2,5-Dihydro-3,6-dimethoxy-2-isopropyl-5-(4'-bromo-2',5'-difluorobenzyl)pyrazine The title compound (1.61 g) was prepared from 0.865 g (4.7 mmol) of (2S)-2,5-dihydro-3,6-dimethoxy-2-isopropylpyrazine and 1.5 g (5.2 mmol) of 4-bromo-2,5-difluorobenzyl) bromide using the procedure described for Intermediate 2, Step A. $^1$H NMR (400 MHz, CDCl$_3$) δ 7.21 (m, 1H), 6.97 (m, 1H), 4.25 (m, 1H), 3.78 (s, 3H), 3.70–3.64 (m, 4H), 3.25–3.18 (m, 1H), 2.96–2.90 (m, 1H), 2.25–2.16 (m, 1H), 1.01 (d, 3H, J=8 Hz), 0.65 (d, 3H, J=8 Hz).

Step C. (R)-N-(1,1-Dimethylethoxycarbonyl)-4-bromo-2,5-difluorophenylalanine Methyl Ester To a solution of 1.61 g (4.14 mmol) of (2S, 5R)-2,5-dihydro-3,6-dimethoxy-2-isopropyl-5-(4'-bromo-2',5'-difluorobenzyl)pyrazine in 10 mL of acetonitrile was added 10 mL of 2N hydrochloric acid. The reaction was stirred for 16 h and concentrated in vacuo. The residue was dissolved in 30 mL of dichloromethane and 5.6 mL (40 mmol) of triethylamine and 2.2 g (10 mmol) of di-tert-butyldicarbonate were added. The reaction was stirred for 16 h, diluted with ethyl acetate and washed sequentially with saturated aqueous sodium bicarbonate solution and brine. The organic phase was dried over magnesium sulfate, concentrated in vacuo and purified by flash chromatography (silica gel, 9:1 hexanes:ethyl acetate) to afford 1.22 g of the title compound. $^1$H NMR (400 MHz, CDCl$_3$) δ 7.27–7.15 (m, 1H), 6.98–6.93 (m, 1H), 5.08 (bs, 1H), 4.61–4.55 (m, 1H), 3.78 (s, 3H), 3.23–3.18 (m, 1H), 3.05–2.95 (m, 1H), 1.41 (s, 9H).

Step D. (R)-N-(1,1-Dimethylethoxycarbonyl)-4-bromo-2,5-difluorophenylalanine

The title compound (1.34 g) was prepared from 1.4 g (3.5 mmol) of (R)-N-(1,1-dimethylethoxycarbonyl)-4-bromo-2,5-diifluorophenylalanine methyl ester using the procedure described for Intermediate 2, Step C. MS (M+1) 380.3 and 382.3.

Step E. (3R)-3-[(1,1-Dimethylethoxycarbonyl)amino]-4-(4'-bromo-2',5'-difluorophenyl)butanoic Acid The title compound (0.36 g) was prepared from 0.6 g (1.57 mmol) of (R)-N-(1,1-dimethylethoxycarbonyl)-4-bromo-2,5-diifluorophenylalanine using the procedure described for Intermediate 3, Step D. MS (M+1) 394.1 and 396.1.

EXAMPLE 1

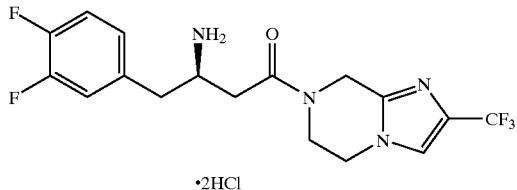

•2HCl

7-[(3R)-3-Amino-4-(3,4-difluorophenyl)butanoyl]-2-(trifluoromethyl)-5,6,7,8-tetrahydroimidazo[1,2-α]pyrazine, dihydrochloride Step A. 2-(Trifluoromethyl)imidazo[1,2-α]pyrazine To a solution of 2-aminopyrazine (5.25 g, 55.2 mmol) in ethanol (120 mL) was added 1-bromo-3,3,3-trifluoroacetone (5.73 mL, 55.2 mmol). The reaction was stirred at reflux for 20 h. After evaporation of solvent, the residue was partitioned between ethyl acetate and saturated aqueous sodium bicarbonate solution. The aqueous layer was extracted with ethyl acetate (3×). The combined organic phase was washed with brine, dried over magnesium sulfate and concentrated. The residue was purified by flash chromatography (silica gel, 1:1 ethyl acetate:hexane, then 100% ethyl acetate) to give 2.35 g of the title compound as a solid. $^1$H NMR (500 MHz, CDCl$_3$) δ 8.02 (m, 2H), 8.13(m, 1H), 9.22 (s, 1H). ESI-MS 188 (M+1).

Step B. 2-(Trifluoromethyl)-5,6,7,8-tetrahydroimidazo[1,2-α]pyrazine

To a solution of 2-(trifluoromethyl)imidazo[1,2-α] pyrazine (2.0 g, 10.46 mmol, from Step A) in methanol (100 mL) was added 10% palladium on carbon (400 mg). The mixture was stirred under atmospheric hydrogen at ambient temperature for 14 h. The mixture was filtered through Celite and washed with methanol (3×). The filtrate was concentrated and purified by flash chromatography (silica gel, 10% methanol in ethyl acetate, then 15% methanol in chloroform with 1% aqueous ammonium hydroxide) to give 1.33 g of the title compound as a solid. $^1$H NMR (500 MHz, CDCl$_3$) δ 1.93 (bs, 1H), 3.26 (t, 2H, J=5.5 Hz), 3.99 (t, 2H, J=5.5 Hz), 4.10 (s, 1H), 7.16 (s, 1H). ESI-MS 192 (M+1).

Step C. 7-[(3R)-3-[(1,1-dimethylethoxycarbonyl)amino]-4-(3,4-difluorophenyl)butanoyl]-2-(trifluoromethyl)-5,6,7,8-tetrahydroimidazo[1,2-α]pyrazine To a solution of 2-(trifluoromethyl)-5,6,7,8-tetrahydroimidazo[1,2-α]pyrazine (64.3 mg, 0.34 mmol, from Step B) and (3R)-3-[(1,1-dimethylethoxycarbonyl) amino]-4-(3,4-difluorophenyl)butanoic acid (105.9 mg, 0.34 mmol) in dichloromethane (5 mL) was added HOBT (54.5 mg, 0.42 mmol) at 0° C. The reaction was stirred at 0° C. for 10 min, then EDC (96.6 mg, 0.50 mmol) was added. After removal of the ice-bath, the reaction was allowed to stir at ambient temperature for 14 h. The mixture was concentrated and purified by HPLC (Gilson; YMC-Pack Pro C18 column, 100×20 mm I.D.; solvent gradient from 10% acetonitrile, 90% water, and 0.1% trifluoroacetic acid to 90% acetonitrile, 10% water, and 0.1% trifluoroacetic acid) to give 115 mg of the title compound as a foamy solid. $^1$H NMR (500 MHz, CDCl$_3$) δ 1.36 (s, 9H), 2.62 (m, 2H), 2.86 (m, 2H) 3.34 (bs, 1H), 3.86 (m, 1H), 4.05 (m, 4H). 4.85 (m, 1H) 5.30–5.38 (m, 1H) 6.97 (m, 3H), 7.28 (m, 1H). LC/MS 489 (M+1).

Step D. 7-[(3R)-3-Amino-4-(3,4-difluorophenyl)butanoyl]-2-(trifluoromethyl)-5,6,7,8-tetrahydroimidazo[1,2-α] pyrazine, dihydrochloride To 7-[(3R)-3-[(1,1-dimethylethoxycarbonyl)amino]-4-(3, 4-difluorophenyl)butanoyl]-2-(trifluoromethyl)-5,6,7,8-tetrahydroimidazo[1,2-α]pyrazine (110.8 mg, 0.226 mmol, from Step C) was added 2 mL of methanol saturated with hydrogen chloride. The reaction was stirred at ambient temperature for 1 h. Concentration gave 89.5 mg of the title compound as a foamy solid. $^1$H NMR (500 MHz, CD$_3$OD) δ 2.97–3.10 (m, 4H), 3.91–4.34 (m, 5H), 4.90–5.04 (m, 2H), 7.16–7.33 (m, 2H), 8.01–8.08 (m, 1H). ESI-MS 389 (M+1).

EXAMPLE 2

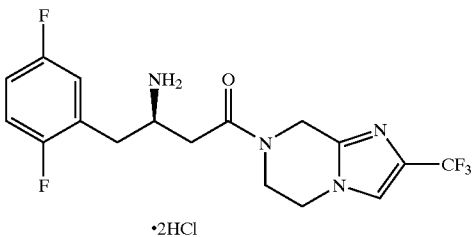

•2HCl

7-[(3R)-3-Amino-4-(2,5-difluorophenyl)butanoyl]-2-(trifluoromethyl)-5,6,7,8-tetrahydroimidazo[1,2-α]pyrazine, dihydrochloride Step A. 7-[(3R)-3-[(1,1-dimethylethoxycarbonyl)amino]-4-(2,5-difluorophenyl)butanoyl]-5,6,7,8-tetrahydroimidazo[1,2-α]pyrazine The title compound was prepared from 2-(trifluoromethyl)-5,6,7,8-tetrahydroimidazo[1,2-α] pyrazine (277 mg, 1.45 mmol, from Example 1, Step B), (3R)-3-[(1,1-dimethylethoxycarbonyl)amino]-4-(2,5-difluorophenyl)butanoic acid (Intermediate 1, 416 mg, 1.32 mmol), DIPEA (226 mg, 1.58 mol), HOBT (216 mg, 1.98 mol) and HATU (753 mg, 1.98 mol) in DMF (6 mL), using a procedure analogous to that described in Example 1 Step C, except for the purification method. The compound was purified by preparative TLC (silica gel, 20% hexane in ethyl acetate, then 10% methanol in dichloromethane) to give 360 mg of the title compound as a foamy solid. $^1$H NMR (500 MHz, CDCl$_3$) δ 1.35 (s, 9H), 2.62 (m, 2H), 2.88 (m, 2H) 3.88–4.16 (m, 5H), 4.73 (s, 1H), 4.85 (m, 1H) 5.26–5.39 (m, 1H) 6.90 (bs, 1H), 7.06(m, 2H), 7.24(m, 1H). ESI-MS 489 (M+1).

Step B. 7-[(3R)-3-Amino-4-(2,5-difluorophenyl)butanoyl]-5,6,7,8-tetrahydroimidazo[1,2-α]pyrazine, dihydrochloride The title compound was prepared from 7-[(3R)-3-[(1,1-dimethylethoxycarbonyl)-amino]-4-(2,5-difluorophenyl)butanoyl]-5,6,7,8-tetrahydroimidazo[1,2-α]pyrazine (349.8 mg, 0.72 mol, from Step A) in 1.5 mL of methanol saturated with hydrogen chloride, using a procedure analogous to that described in Example 1, Step D. Evaporation of solvent gave 299 mg of the title compound as a foamy solid. $^1$H NMR (500 MHz, CD$_3$OD): δ 3.10–3.17 (m, 2H), 2.89–2.99 (m, 2H), 3.94–4.22 (m, 4H), 4.33 (m, 1H), 4.91–5.48 (m, 2H), 7.07–7.23 (m, 3H), 8.05 (m, 1H). ESI-MS 389(M+1).

EXAMPLE 3

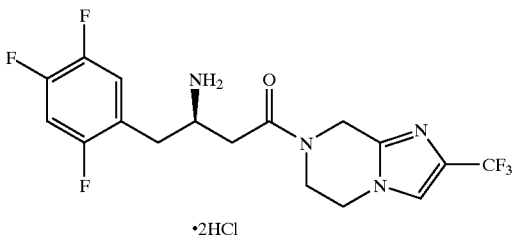

•2HCl

7-[(3R)-3-Amino-4-(2,4,5-trifluorophenyl)butanoyl]-2-(trifluoromethyl)-5,6,7,8-tetrahydroimidazo[1,2-α]pyrazine, dihydrochloride Step A. 7-[(3R)-3-[(1,1-dimethylethoxycarbonyl)amino]-4-(2,4,5-trifluorophenyl)butanoyl]-5,6,7,8-tetrahydroimidazo[1,2-α]pyrazine The title compound was prepared from 2-(trifluoromethyl)-5,6,7,8-tetrahydroimidazo[1,2-α] pyrazine (31.7 mg, 0.166 mmol, from Example 1, Step B), (3R)-3-[(1,1-dimethylethoxycarbonyl)amino]-4-(2,4,5-trifluorophenyl)butanoic acid (Intermediate 3, 57 mg, 0.166 mmol), HOBT (26.9 mg,0.199 ) mmol, and EDC (47.8 mg, 0.249 mmol) in 4 mL of dichloromethane, using a procedure analogous to that described in Example 1, Step C. Purification by preparative TLC (silica gel, 100% ethyl acetate, then 10% methanol in dichloromethane) gave 40 mg of the title compound as a foamy solid. $^1$H NMR (500 MHz, CDCl$_3$) δ 1.35 (s, 9H), 3.00 (m, 2H), 3.30 (m, 2H), 3.93 (m, 1H) 4.04–4.24 (m, 2H), 4.23 (s, 1H), 4.35 (m, 1H) 4.97–5.48 (m, 2H) 7.22 (m, 1H), 7.44 (m, 1H), 8.04 (m, 1H). ESI-MS 507 (M+1).

Step B. 7-[(3R)-3-Amino-4-(2,4,5-trifluorophenyl) butanoyl]-5,6,7,8-tetrahydroimidazo[1,2-α]pyrazine, dihydrochloride The title compound was prepared from 7-[(3R)-3-[(1,1-dimethylethoxycarbonyl)amino]-4-(2,4,5-trifluorophenyl) butanoyl]-5,6,7,8-tetrahydroimidazo[1,2-α]pyrazine (38 mg, 0.075 mmol, from Step A), in 1.5 mL of methanol saturated with hydrogen chloride, using a procedure analogous to that described in Example 1, Step D. Evaporation of solvent gave 34 mg of the title compound as a foamy solid. $^1$H NMR (500 MHz, CD$_3$OD): δ 2.59–2.66 (m, 2H), 2.92 (m, 2H), 3.89–4.16–4.22 (m, 5H), 4.70–4.84 (m, 2H), 5.42 (m, 1H), 6.86 (m, 1H), 7.06 (m, 1H), 7.24 (m, 1H). ESI-MS 407(M+1).

EXAMPLE 4

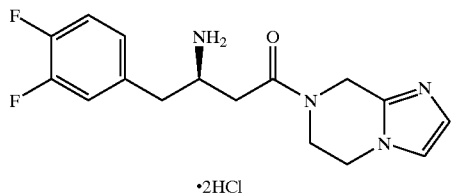

•2HCl

7-[(3R)-3-Amino-4-(3,4-difluorophenyl)butanoyl]-5,6,7,8-tetrahydroimidazo[1,2-α]pyrazine, dihydrochloride Step A. Imidazo[1,2-α]pyrazine To a solution of 2-aminopyrazine (2.0 g, 21.03 mmol) in ethanol (40 mL) was added 2-bromo-1,1-dimethoxyethane (2.5 mL, 21.03 mmol) followed by 5 drops of concentrated hydrochloric acid. After refluxing for 14 hours, the solvent was evaporated. The residue was partitioned between ethyl acetate and saturated aqueous sodium bicarbonate solution. The aqueous layer was extracted with ethyl acetate (3x). The combined organic phase was washed with brine, dried over magnesium sulfate, and concentrated. The residue was purified by flash chromatography (100% ethyl acetate, 10% methanol in ethyl acetate, then 10% methanol in dichloromethane) to give 536 mg of the title compound as a solid. $^1$H NMR (500 MHz, CDCl$_3$) δ 7.70 (bs, 1H), 7.82 (bs, 1H), 7.89 (d, 1H, J=4.4 Hz), 8.10 (d, 1H, J=4.6 Hz), 9.12 (s, 1H).

Step B. 5,6,7,8-Tetrahydroimidazo[1,2-α]pyrazine

The title compound was prepared from imidazo[1,2-α] pyrazine (500 mg, 4.20 mmol, from Step A) and platinum oxide (250 mg) in methanol (50 mL), using a procedure analogous to that described in Example 1, Step B. Concentration gave the title compound (512 mg) as a viscous oil. $^1$H NMR (500 MHz, CD$_3$OD) δ 3.37 (t, 1H, J=5.5 Hz), 4.18 (t, 2H, J=5.6 Hz), 4.88 (s, 1H), 7.27 (d, J=1.6 Hz, 1H), 7.33 (d, 1H).

Step C. 7-[(3R)-3-[(1,1-dimethylethoxycarbonyl)amino]-4-(3,4-difluorophenyl)butanoyl]-5,6,7,8-tetrahydroimidazo[1,2-α]pyrazine The title compound was prepared from 5,6,7,8-tetrahydroimidazo[1,2-α]pyrazine (31.3 mg, 0.254 mmol, from Step B), (3R)-3-[(1,1-dimethylethoxycarbonyl)amino]-4-(3,4-difluorophenyl)butanoic acid (80 mg, mmol), DIPEA (32.8 mg, 0.254 mmol), HOBT (41.2 mg, 0.305 mmol) and EDC (73 mg, 0.381 mmol) in 5 mL of dichloromethane, using a procedure analogous to that described in Example 1, Step C. Purification by HPLC (Gilson; YMC-Pack Pro C18 column, 100×20 mm I.D.; solvent gradient system from 10% acetonitrile, 90% water, and 0.1% trifluoroacetic acid to 90% acetonitrile, 10% water, and 0.1% trifluoroacetic acid) gave 75 mg of the title compound as a viscous oil. $^1$H NMR (500 MHz, CDCl$_3$) δ 1.38 (s, 9H), 2.05 (bs, 1H), 2.62 (m, 2H), 2.89 (m, 2H) 3.81–4.04 (m, 5H), 4.64–4.88 (m, 2H). 5.38 (m, 1H) 6.88 (m, 2H), 7.05(m, 3H). ESI-MS 421 (M+1).

Step D. 7-[(3R)-3-Amino-4-(3,4-difluorophenyl)butanoyl]-5,6,7,8-tetrahydroimidazo[1,2-α]pyrazine, dihydrochloride The title compound was prepared from 7-[(3R)-3-[(1,1-dimethylethoxycarbonyl)amino]-4-(3,4-difluorophenyl)butanoyl]-5,6,7,8-tetrahydroimidazo[1,2-α]pyrazine (72 mg, 0.171 mmol, from Step C), in 1.5 mL of methanol saturated with hydrogen chloride, using a procedure analogous to that described in Example 1, Step D. Concentration gave 66 mg of the title compound as a foamy solid. $^1$H NMR (500 MHz, CD$_3$OD) δ 2.96–3.13 (m, 4H), 3.93 (m, 1H), 4.13 (m, 2H), 4.26–4.38 (m, 2H), 4.26–4.38 (m, 2H), 4.90–5.04 (m, 2H), 7.19–7.36 (m, 3H), 7.58 (m, 1H). ESI-MS 321 (M+1).

EXAMPLE 5

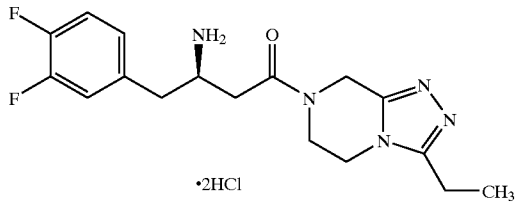

7-[(3R)-3-Amino-4-(3,4-difluorophenyl)butanoyl]-3-ethyl-5,6,7,8-tetrahydro-1,2,4-triazolo[4,3-α]pyrazine, dihydrochloride Step A. 8-Chloro-3-ethyl-1,2,4-triazolo[4,3-α]pyrazine To 3-chloro-2-hydrazinopyrazine (3.0 g, 20.75 mmol), prepared from 2,3-dichloropyrazine and hydrazine using a procedure analogous to that described in the literature (Huynh-Dinh et al, *J. Org. Chem.* 1979, 44, 1028), was added 8 mL of triethyl orthopropionate. After refluxing for 10 h, the reaction was cooled down to ambient temperature and the precipitate was filtered. The solid was purified by flash chromatography (100% ethyl acetate, then 10% methanol in ethyl acetate) to give 2.73 g of the title compound as a solid. $^1$H NMR (500 MHz, CDCl$_3$) δ 1.54 (t, 3H, J=7.6 Hz), 3.16 (q, 2H, J=7.8 Hz), 7.70 (d, 1H, J=4.5 Hz), 7.83 (d, 1H, J=4.8 Hz).

Step B. 3-Ethyl-5,6,7,8-tetrahydro-1,2,4-triazolo[4,3-α]pyrazine, hydrochloride

The title compound was prepared from 8-chloro-3-ethyl-1,2,4-triazolo[4,3-α]pyrazine (2.70 g, 14.8 mmol, from Step A) and platinum oxide (0.4 g) in 200 mL of methanol in a paar shaker under hydrogen (50 psi) for 14 hours. Filtration through Celite followed by concentration gave the title compound as a solid. $^1$H NMR (500 MHz, CD$_3$OD) δ 1.36 (t, 3H, J=6.0 Hz), 2.84 (q, 2H, J=6.0 Hz), 3.70 (t, 2H, J=8.0 Hz), 4.28 (t, 2H, J=8.0 Hz). 4.06(s, 2H). ESI-MS 153 (M+1).

Step C. 7-[(3R)-3-[(1,1-dimethylethoxycarbonyl)amino]-4-(3,4-difluorophenyl)butanoyl]-3-ethyl-5,6,7,8-tetrahydro-1,2,4-triazolo[4,3-α]pyrazine The title compound was prepared from 3-ethyl-5,6,7,8-tetrahydro-1,2,4-triazolo[4,3-α]pyrazine hydrochloride (400 mg, 2.12 mmol, from Step B), (3R)-3-[(1,1-dimethylethoxycarbonyl)amino]-4-(3,4-difluorophenyl) butanoic acid (668 mg, 2.12 mmol), DIPEA (1.1 mL, 4.24 mmol), HOBT (343.8 mg, 2.54 mmol) and EDC (609.6 mg, 3.18 mmol) in 20 mL of dichloromethane, using a procedure analogous to that described in Example 1, Step C. The crude product was purified by HPLC (Gilson; YMC-Pack Pro C18 column, 100×20 mm I.D.; solvent gradient from 10% acetonitrile, 90% water, and 0.1% trifluoroacetic acid to 90% acetonitrile, 10% water, and 0.% trifluoroacetic acid) to give 366.3 mg of the title compound as a viscous oil. $^1$H NMR (500 MHz, CDCl$_3$) δ 1.31–1.34 (m, 12H), 2.67–2.92 (m, 6H), 4.03–4.12 (m, 4H), 5.03–5.31 (m, 3H), 6.93 (s, 1H), 7.05 (m, 2H). ESI-MS 450 (M+1).

Step D. 7-[(3R)-3-Amino-4-(3,4-difluorophenyl)butanoyl]-3-ethyl-5,6,7,8-tetrahydro-1,2,4-triazolo[4,3-α]pyrazine, dihydrochloride The title compound was prepared from 7-[(3R)-3-[(1,1-dimethylethoxycarbonyl)-amino]-4-(3,4-difluorophenyl)butanoyl]-3-ethyl-5,6,7,8-tetrahydro-1,2,4-triazolo[4,3-α]pyrazine (30 mg, 0.067 mmol from Step C), in 1.5 mL of methanol saturated with hydrogen chloride, using a procedure analogous to that described in Example 1, Step D. Evaporation of solvent afforded 28 mg of the title compound as a viscous oil. $^1$H NMR (500 MHz, CD$_3$OD) δ 1.45 (t, 3H), 2.93–3.07 (m, 6H), 3.90–4.31 (m, 5H), 5.08 (m, 2H), 7.16 (s, 1H), 7.31 (m, 2H). ESI-MS 350 (M+H).

EXAMPLE 6

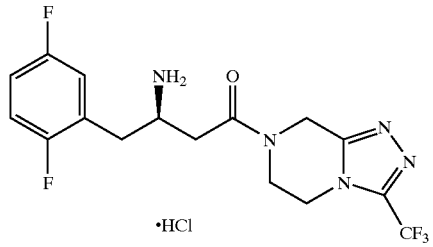

7-[(3R)-3-Amino-4-(2,5-difluorophenyl)butanoyl]-3-(trifluoromethyl)-5,6,7,8-tetrahydro-1,2,4-triazolo[4,3-α] pyrazine, hydrochloride Step A. 3-(Trifluoromethyl)-1,2,4-triazolo[4,3-α]pyrazine A mixture of 2-hydrazinopyrazine (820 mg, 7.45 mmol), prepared from 2-chloropyrazine and hydrazine using a procedure analogous to that described in the literature (P. J. Nelson and K. T. Potts, *J. Org. Chem.* 1962, 27, 3243, except that the crude product was extracted into 10% methanol/dichloromethane and filtered, and the filtrate was concentrated and purified by flash chromatography on silica gel, eluting with 100% ethyl acetate followed by 10% methanol in dichloromethane), TFA (2.55 g, 22.4 mmol), and polyphosphoric acid (10 mL) was heated to 140° C. with stirring for 18 h. The solution was added to ice and neutralized by the addition of ammonium hydroxide. The aqueous solution was extracted with ethyl acetate (3×), washed with brine, and dried over anhydrous magnesium sulfate. Concentration followed by flash chromatography (silica gel, 1:1 hexane- :ethyl acetate, then 100% ethyl acetate) afforded the title compound as a solid (861 mg). $^1$H NMR (500 MHz, CDCl$_3$) δ 8.17–8.20 (m, 2H), 9.54 (s, 1H). LC/MS (M+1) 189.

Step B. 3-(Trifluoromethyl)-5,6,7,8-tetrahydro-1,2,4-triazolo[4,3-α]pyrazine 3-(Trifluoromethyl)-1,2,4-triazolo[4,3-α] pyrazine (540 mg, 2.87 mmol, from Step A) was hydrogenated under atmospheric hydrogen with 10% Pd/C (200 mg) as a catalyst in ethanol (10 mL) at ambient temperature for 18 h. Filtration through Celite followed by concentration gave a dark colored oil. Dichloromethane was added to the above oil and the insoluble black precipitate was filtered off. Concentration of the filtrate gave the title compound as an oil (495 mg). $^1$H NMR (500 MHz, CDCl$_3$) δ 2.21 (br, 1H), 3.29 (t, 2H, J=5.5 Hz), 4.09 (t, 2H, J=5.5 Hz), 4.24 (s, 2H). LC/MS (M+1) 193.

Step C. 7-[(3R)-3-[(1,1-Dimethylethoxycarbonyl)amino]-4-(2,5-difluorophenyl)butanoyl]-3-(trifluoromethyl)-5,6,7,8-tetrahydro-1,2,4-triazolo[4,3-α]pyrazine The title compound was prepared from (3R)-3-[(1,1-dimethylethoxycarbonyl)-amino]-4-(2,5-difluorophenyl) butanoic acid (Intermediate 1, 50 mg, 0.16 mmol) and 3-(trifluoromethyl)-5,6,7,8-tetrahydro-1,2,4-triazolo[4,3-α] pyrazine (30 mg, 0.16 mmol) using a procedure analogous to that described for Example 1, Step C. The crude product was purified by preparative TLC (silica gel, 100% ethyl acetate, then 10% methanol/dichloromethane (2×)) to afford the title compound (38.1 mg) as a solid. $^1$H NMR (500 MHz, CDCl$_3$) δ 1.38 (s, 9H), 2.57~3.05 (m, 4H), 3.85~4.30 (m, 5H), 4.90 (s, 1H), 4.95~5.15 (m, 1H), 5.22~5.40 (br, 1H), 6.86~7.24 (m, 3H). LC/MS (M+1-t-Boc) 390.

Step D. 7-[(3R)-3-Amino-4-(2,5-difluorophenyl)butanoyl]-3-(trifluoromethyl)-5,6,7,8-tetrahydro-1,2,4-triazolo[4,3-α] pyrazine, hydrochloride The title compound was prepared from 7-[(3R)-3-[(1,1-dimethylethoxycarbonyl)-amino]-4-(2,5-difluorophenyl) butanoyl]-3-(trifluoromethyl)-5,6,7,8-tetrahydro-1,2,4-triazolo[4,3-α]pyrazine (19.1 mg, 0.039 mmol, from Step C) using a procedure analogous to that described for Example 1, Step D. Concentration afforded the title compound (16.1 mg) as a solid. $^1$H NMR (500 MHz, CD$_3$OD) δ 2.75–3.16 (m, 4H), 3.86~4.35 (m, 5H), 4.95~5.05 (m, 2H), 7.03~7.20 (m, 3H) LC/MS (M+1) 390.

EXAMPLE 7

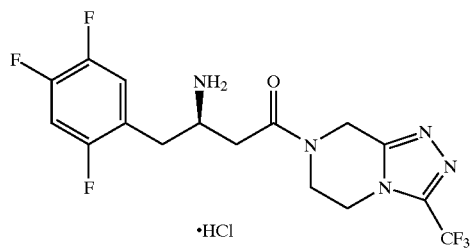

7-[(3R)-3-Amino-4-(2,4,5-trifluorophenyl)butanoyl]-3-(trifluoromethyl)-5,6,7,8-tetrahydro-1,2,4-triazolo[4,3-α] pyrazine, hydrochloride Step A. 7-[(3R)-3-[(1,1-Dimethylethoxycarbonyl)amino]-4-(2,4,5-trifluorophenyl)-butanoyl]-3-(trifluoromethyl)-5,6,7,8-tetrahydro-1,2,4-triazolo[4,3-α]pyrazine The title compound was prepared from (3R)-3-[(1,1-dimethylethoxy-carbonyl)-amino]-4-(2,4,5-trifluorophenyl) butanoic acid (Intermediate 3, 50.1 mg, 0.15 mmol) and 3-(trifluoromethyl)-5,6,7,8-tetrahydro-1,2,4-triazolo[4,3-α] pyrazine (39.2 mg, 0.20 mmol) using a procedure analogous to that described for Example 1, Step C. The crude product was purified by preparative TLC (silica gel, 100% ethyl acetate) to afford the title compound (29 mg) as a solid. $^1$H NMR (500 MHz, CDCl$_3$) δ 1.37 (s, 9H), 2.61~3.00 (m, 4H), 3.92~4.30 (m, 5H), 4.93 (s, 1H), 4.95~5.12 (m, 1H), 5.22~5.35 (br, 1H), 6.83~6.95 (m, 1H), 7.02~7.12 (m, 1H). LC/MS (M+1-t-Bu) 452.

Step B. 7-[(3R)-3-Amino-4-(2,4,5-trifluorophenyl) butanoyl]-3-(trifluoromethyl)-5,6,7,8-tetrahydro-1,2,4-triazolo[4,3-α] pyrazine, hydrochloride The title compound was prepared from 7-[(3R)-3-[(1,1-dimethylethoxycarbonyl)-amino]-4-(2,4,5-trifluorophenyl) butanoyl]-3-(trifluoromethyl)-5,6,7,8-tetrahydro-1,2,4-triazolo[4,3-α]pyrazine (22 mg, 0.039 mmol, from Step A) using a procedure analogous to that described for Example 1, Step D. Concentration afforded the title compound (16.5 mg) as a solid. $^1$H NMR (500 MHz, CD$_3$OD) δ 2.75~3.15 (m, 4H), 3.82~4.35 (m, 5H), 4.90~5.05 (m, 2H), 7.16~7.25 (m, 1H), 7.30~7.42 (m, 1H). LC/MS (M+1) 408.

Essentially following the procedures outlined for Examples 1–7, the compounds listed in Table 1 were prepared.

TABLE 1

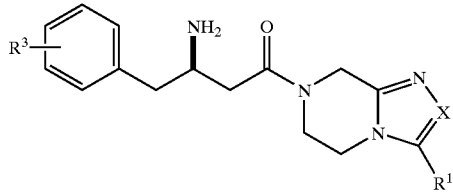

| Example | R$^3$ | X | R$^1$ | MS (M + 1) |
|---|---|---|---|---|
| 8 | 2-F | C-Et | H | 331 |
| 9 | 3-F, 4-F | C-Et | H | 349 |
| 10 | 2-F | CH | H | 303 |
| 11 | 2-F | C—CF$_3$ | H | 371 |
| 12 | 3-F, 4-F | C-(4-F—Ph) | H | 415 |
| 13 | 3-F, 4-F | C—Ph | H | 397 |
| 14 | 3-F, 4-F | C-(4-OMe—Ph) | H | 427 |
| 15 | 3-F, 4-F | C-(3-F, 4-F—Ph) | H | 433 |
| 16 | 3-F, 4-F | C-(4-OCF$_3$—Ph) | H | 481 |
| 17 | 3-F, 4-F | C—C$_2$F$_5$ | H | 439 |

TABLE 1-continued

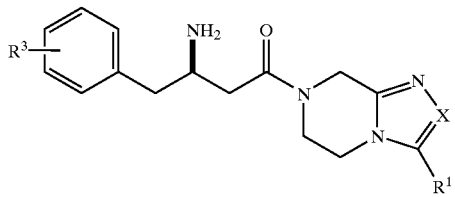

| Example | $R^3$ | X | $R^1$ | MS (M + 1) |
|---|---|---|---|---|
| 18 | 2-F | N | Et | 352 |
| 19 | 3-F, 4-F | N | Et | 336 |
| 20 | 2-F | N | Me | 318 |
| 21 | 2-F, 5-F | N | Et | 350 |
| 22 | 2-F | N | H | 304 |
| 23 | 3-F, 4-F | N | H | 322 |
| 24 | 3-F, 4-F | N | $CF_3$ | 390 |
| 25 | 2-F, 4-$CF_3$ | N | $CF_3$ | 440 |
| 26 | 3-F, 4-F | N | $CH_2CF_3$ | 404 |
| 27 | 2-F, 5-F | N | $CH_2CF_3$ | 404 |
| 28 | 2-F | CH | $CH_2Ph$ | 393 |
| 29 | 2-F | CH | Ph | 379 |
| 30 | 2-F, 4-$CF_3$ | C—$CF_3$ | H | 439 |
| 31 | 2-F, 4-F, 5-F | C—$CF_2CF_3$ | H | 379 |
| 32 | 4-Br, 2-F, 5-F | C—$CF_3$ | H | 467, 469 |
| 33 | 4-Br, 2-F, 5-F | N | $CF_3$ | 468, 470 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

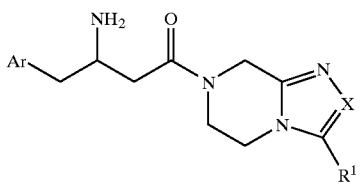

wherein:

Ar is phenyl which is unsubstituted or substituted with 1–5 of $R^3$, wherein $R^3$ is independently selected from the group consisting of:
  (1) halogen,
  (2) $C_{1-6}$alkyl, which is linear or branched and is unsubstituted or substituted with 1–5 halogens,
  (3) $OC_{1-6}$alkyl, which is linear or branched and is unsubstituted or substituted with 1–5 halogens, and
  (4) CN;

X is selected from the group consisting of:
  (1) N, and
  (2) $CR^2$;

$R^1$ and $R^2$ are independently selected from the group consisting of:
  (1) hydrogen,
  (2) CN,
  (3) $C_{1-10}$alkyl, which is linear or branched and which is unsubstituted or substituted with 1–5 halogens or phenyl, which is unsubstituted or substituted with 1–5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched,
  (4) phenyl which is unsubstituted or substituted with 1–5 substituents independently selected from halogen, CN, OH, $R^4$, $OR^4$, $NHSO_2R^4$, $SO_2R^4$, $CO_2H$, and $CO_2C_{1-6}$alkyl, wherein the $CO_2C_{1-6}$alkyl is linear or branched, and
  (5) a 5- or 6-membered heterocycle which may be saturated or unsaturated comprising 1–4 heteroatoms independently selected from N, S and O, the heterocycle being unsubstituted or substituted with 1–3 substituents independently selected from oxo, OH, halogen, $C_{1-6}$alkyl, and $OC_{1-6}$alkyl, wherein the $C_{1-6}$alkyl and $OC_{1-6}$alkyl are linear or branched and optionally substituted with 1–5 halogens;

$R^4$ is $C_{1-6}$alkyl, which is linear or branched and which is unsubstituted or substituted with 1–5 groups independently selected from halogen, $CO_2H$, and $CO_2C_{1-6}$alkyl, wherein the $CO_2C_{1-6}$alkyl is linear or branched;

and pharmaceutically acceptable salts thereof and individual diastereomers thereof.

2. The compound of claim 1 of the formula Ia:

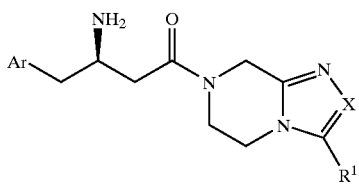

wherein X, Ar and $R_1$ are defined in claim 1;
and pharmaceutically acceptable salts and individual diastereomers thereof.

3. The compound of claim 1 of the formula Ib:

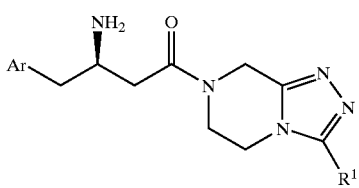

wherein Ar and $R^1$ are defined in claim 1;
and pharmaceutically acceptable salts and individual diastereomers thereof.

4. The compound of claim 1 of the formula Ic:

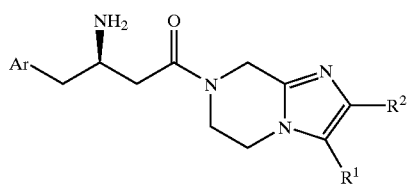

wherein Ar, $R^1$ and $R^2$ are defined in claim 1;
and pharmaceutically acceptable salts thereof and individual diastereomers thereof.

5. The compound of claim 1 wherein Ar is phenyl which is unsubstituted or substituted with 1–5 substitutents which are independently selected from the group consisting of:
(1) fluoro,
(2) bromo, and
(3) $CF_3$.

6. The compound of claim 1 wherein Ar is selected from the group consisting of:
(1) phenyl,
(2) 2-fluorophenyl,
(3) 3,4-difluorophenyl,
(4) 2,5-difluorophenyl,
(5) 2,4,5-trifluorophenyl,
(6) 2-fluoro-4-(trifluoromethyl)phenyl, and
(7) 4-bromo-2,5-difluorophenyl.

7. The compound of claim 1 wherein $R^1$ is selected from the group consisting of:
(1) hydrogen, and
(2) $C_{1-6}$alkyl, which is linear or branched and which is unsubstituted or substituted with phenyl or 1–5 fluoro.

8. The compound of claim 1 wherein $R^1$ is selected from the group consisting of:
(1) hydrogen,
(2) methyl,
(3) ethyl,
(4) $CF_3$,
(5) $CH_2CF_3$,
(5) $CF_2CF_3$,
(6) phenyl, and
(7) benzyl.

9. The compound of claim 1 wherein $R^1$ is selected from the group consisting of:
(1) hydrogen,
(2) methyl,
(3) ethyl,
(4) $CF_3$, and
(5) $CH_2CF_3$.

10. The compound of claim 1 wherein $R^1$ is hydrogen or $CF_3$.

11. The compound of claim 1 wherein $R^2$ is selected from:
(1) hydrogen,
(2) $C_{1-6}$alkyl, which is linear or branched and which is unsubstituted or substituted with 1–5 fluoro and
(3) phenyl, which is unsubstituted or substituted with 1–3 substituents independently selected from fluoro, $OCH_3$, and $OCF_3$.

12. The compound of claim 1 wherein $R^2$ is selected from the group consisting of:
(1) hydrogen,
(2) methyl,
(3) ethyl,
(4) $CF_3$,
(5) $CH_2CF_3$,
(5) $CF_2CF_3$,
(6) phenyl,
(7) (4-methoxy)phenyl,
(8) (4-trifluoromethoxy)phenyl,
(9) 4-fluorophenyl, and
(10) 3,4-difluorophenyl.

13. The compound of claim 1 wherein $R^2$ is $CF_3$ or $CF_2CF_3$.

14. The compound of claim 1 wherein $R^3$ is F, Br or $CF_3$.

15. A compound which is selected from the group consisting of:

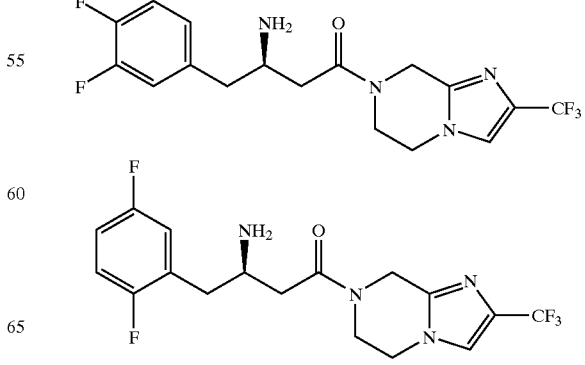

37
-continued
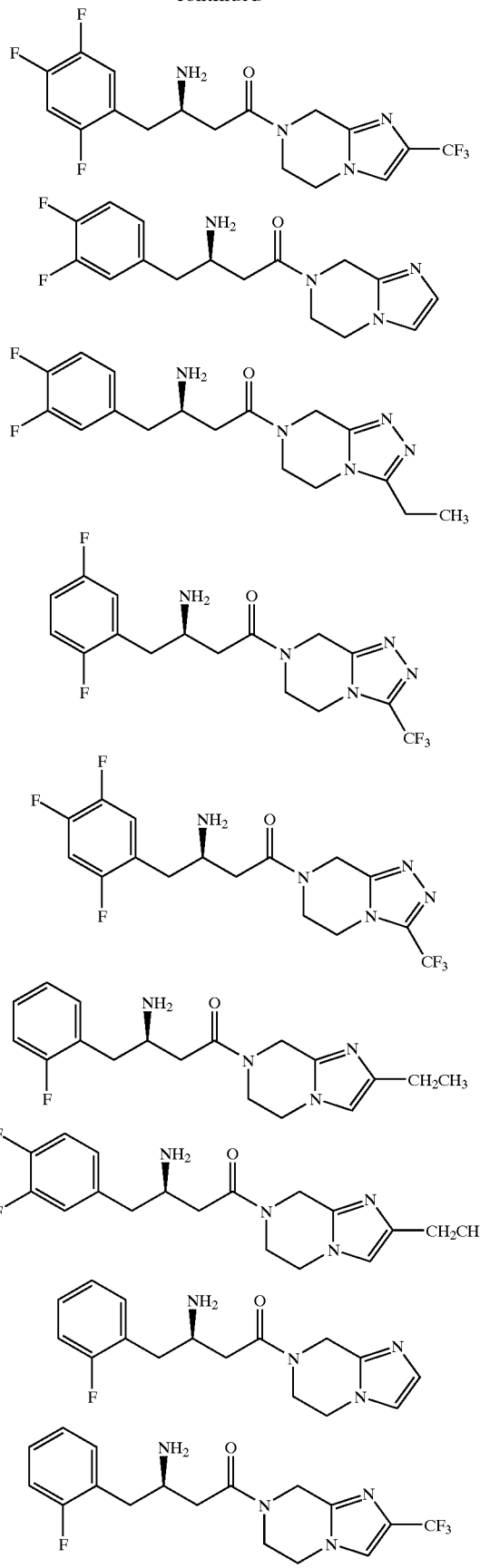
38
-continued
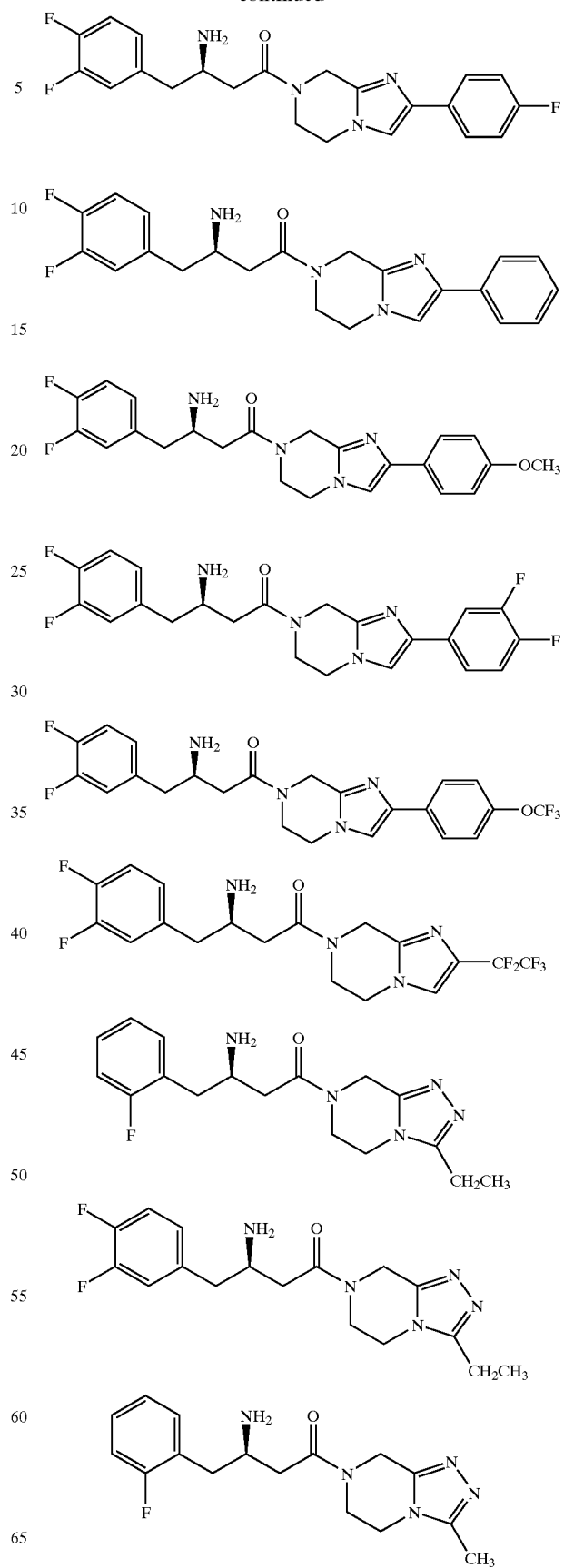

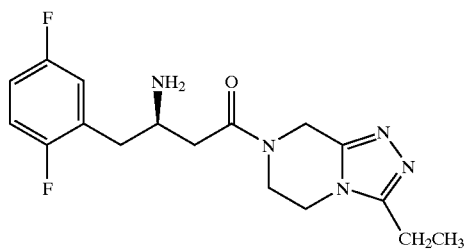
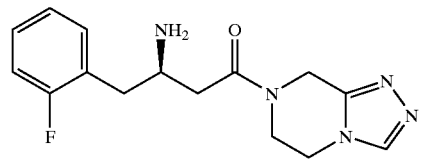
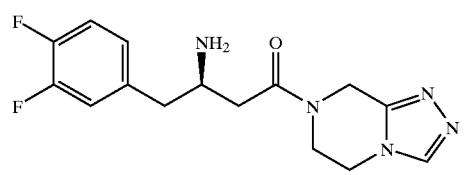
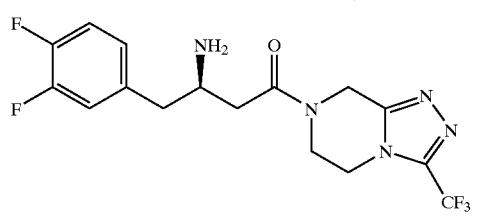
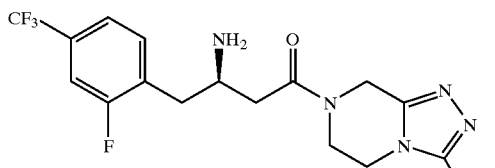
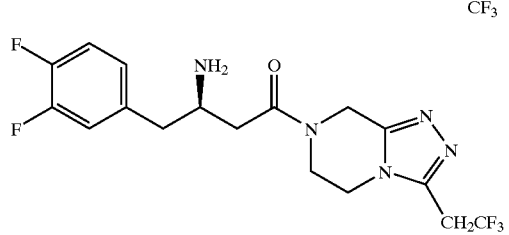
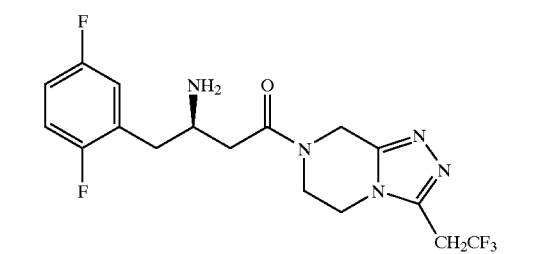
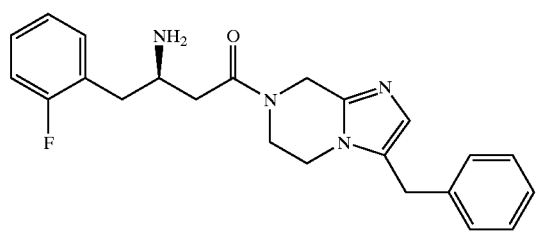
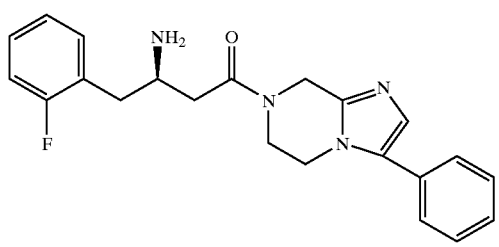
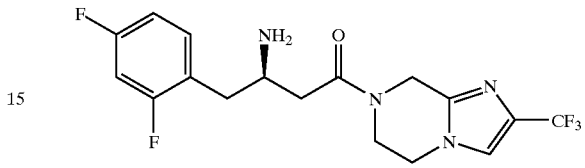
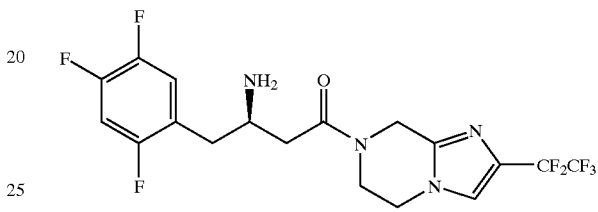
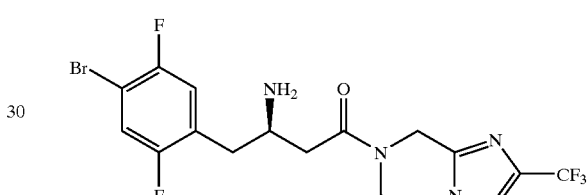
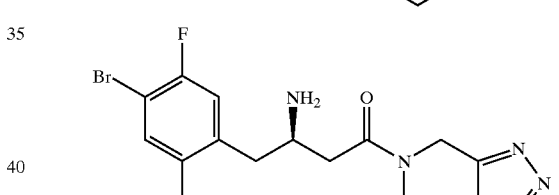
or a pharmaceutically acceptable salts thereof.
16. A compound which is:
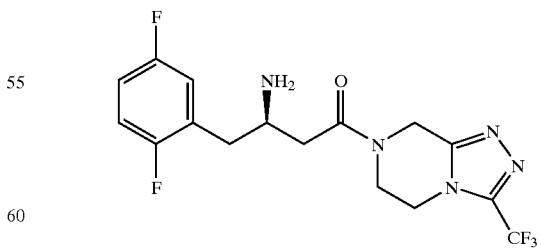
or a pharmaceutically acceptable salt thereof.

17. A compound which is:

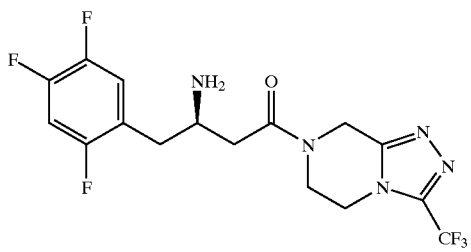

or a pharmaceutically acceptable salt thereof.

18. A pharmaceutical composition which comprises an inert carrier and a compound of claim 1.

19. A pharmaceutical composition which comprises an inert carrier and a compound of claim 16.

20. A pharmaceutical composition which comprises an inert carrier and a compound of claim 16.

21. A method for inhibition of dipeptidyl peptidase-IV enzyme activity in a mammal in need thereof which comprises the administration to the mammal of an effective amount of a compound of claim 1.

22. A method for treating or controlling diabetes in a mammalian patient in need thereof comprising the administration to a patient of an effective amount of a compound of claim 1.

23. A method for treating or controlling non-insulin dependent (Type 2) diabetes mellitus in a mammalian patient in need thereof which comprises administering to the patient a therapeutically effective amount of a compound of claim 1.

24. A method for treating or controlling hyperglycemia in a mammalian patient in need thereof which comprises administering to the patient a therapeutically effective amount of a compound of claim 1.

25. A method for treating or controlling obesity in a mammalian patient in need thereof which comprises administering to the patient a therapeutically effective amount of a compound of claim 1.

26. A method for treating or controlling one or more lipid disorders selected from the group consisting of dyslipidemia, hyperlipidemia, hypertriglyceridemia, hypercholesterolemia, low HDL and high LDL in a mammalian patient in need thereof which comprises administering to the patient a therapeutically effective amount of a compound of claim 1.

* * * * *

UNITED STATES PATENT AND TRADEMARK OFFICE
CERTIFICATE OF CORRECTION

PATENT NO. : 6,699,871 B2
DATED : March 2, 2004
INVENTOR(S) : Scott D. Edmondson et al.

It is certified that error appears in the above-identified patent and that said Letters Patent is hereby corrected as shown below:

<u>Column 40,</u>
Line 48, cancel "salts" and substitute therefor -- salt --.

<u>Column 41,</u>
Line 22, cancel "16" and substitute therefor -- 17 --.

Signed and Sealed this

Fifteenth Day of June, 2004

JON W. DUDAS
*Acting Director of the United States Patent and Trademark Office*